United States Patent [19]

Ryan et al.

[11] Patent Number: 5,168,040

[45] Date of Patent: Dec. 1, 1992

[54] COLORIMETRIC ASSAY FOR DETECTING FUNGAL CELL ENVELOPE PERTURBATIONS

[75] Inventors: Michael J. Ryan, West Milford; Jason A. Lotvin, Union; Elizabeth B. Smith, Plainsboro; Karen J. Shaw, Glen Ridge, all of N.J.

[73] Assignee: Schering Corporation, Kenilworth, N.J.

[21] Appl. No.: 168,831

[22] Filed: Mar. 16, 1988

[51] Int. Cl.$^5$ ............................ C12Q 1/68; C12Q 1/18
[52] U.S. Cl. .................................... 435/6; 435/14; 435/32; 435/172.3; 435/255
[58] Field of Search ............... 435/6, 14, 32, 99, 172.3, 435/182, 254, 255, 942

[56] References Cited

U.S. PATENT DOCUMENTS

| | | | |
|---|---|---|---|
| 4,626,505 | 12/1986 | Falco | 435/256 X |
| 4,745,057 | 5/1988 | Beckage et al. | 435/172.3 X |
| 4,774,173 | 9/1988 | Reinhartz | 435/29 X |

OTHER PUBLICATIONS

Yocum et al., "Use of lacZ Fusions to Delimit Regulatory Elements . . . ", Molec. & Cellular Biol. 4(10), 1985-1998 (Oct. 1984).

Teem et al., "Expression of a β-galactosidase gene containing . . . ", PNAS 80, 4403-4407 (Jul. 1983).

Primary Examiner—Garnette D. Draper
Assistant Examiner—Laurie Scheiner
Attorney, Agent, or Firm—Matthew Boxer; Henry C. Jeanette; James R. Nelson

[57] ABSTRACT

Methods of constructing and using gene expression systems to indicate the pertubation of fungal cell envelopes are provided. The recombinant genes produce indicator cleavage enzymes such as β-galactosidase when galactose is able to enter the cell, despite the presence of glucose, through discontinuous cell envelopes. The indicator cleavage enzymes such as β-galactosidase cleaves a colorimetric indicator placed in the media to produce an easily detected measurement of altered cell envelope permeability.

13 Claims, 5 Drawing Sheets

COLORIMETRIC ASSAY FOR DETECTING FUNGAL CELL ENVELOPE PERTURBATIONS

BACKGROUND OF THE INVENTION

It is well established in microbiology that fungi have cell envelopes composed of a membrane and an outer cell wall. One component of fungal cell walls is a polysaccharide known as chitin (a homopolymer of N-acetyl-D-glucosamine in $\beta(1\rightarrow4)$linkage). Cell walls also contain large amounts of glucan and mannoprotein. Disruptions in the metabolic pathway leading to chitin synthesis or chemical or physical perturbations of the intact cell wall are desirable mechanisms for antifungal agents. Severe weaknesses or large discontinuities in the cell wall may lead to cytoplasmic leakage and cell death. Smaller holes in the cell wall may allow small regions of the cell membrane to "blow out" permitting usually excluded molecules to enter the cell. Consequently, the combination of a usually excluded cytoplasmically active antifungal agent with a localized cell wall perturbating agent can lead to death of the fungal cell.

The ability to screen compounds for cell envelope perturbating activity would be a useful means of identifying antifungal agents as well as understanding the mechanism of cell envelope synthesis and maintenance. The ideal screening system would be sensitive, specific, relatively rapid, and easy to read.

SUMMARY OF THE INVENTION

One aspect of the present invention involves a colorimetric assay for detecting fungal cell envelope perturbations comprising:

a. placing a test compound or test sample being assayed for antifungal activity on or in a culture medium comprising (1) a colorimetric indicator of $\beta$-galactosidase activity, (2) a fungal cell transformed with a vector containing an indicator cleavage enzyme gene downstream from a fungal promoter, (3) an activator material that activates said fungal promoter and causes expression of the indicator cleavage enzyme by the transformed cell, and (4) an inhibitor material such as glucose which inhibits the uptake of said activator material through the cell envelope of said transformed cell in the absence of cell envelope perturbations;

b. incubating the culture for sufficient time to enable activation and expression of $\beta$-galactosidase genes and development of the colorimetric indicator; and c. detecting the development of the indicator in said culture medium.

Other aspects of the invention are the specific plasmids, pTS106 and pTS107 and the transformed fungal cells containing a vector comprising a $\beta$-galactosidase gene downstream from the GAL1 galactose activated fungal promoter.

DETAILED DESCRIPTION OF THE INVENTION

Figure 1:
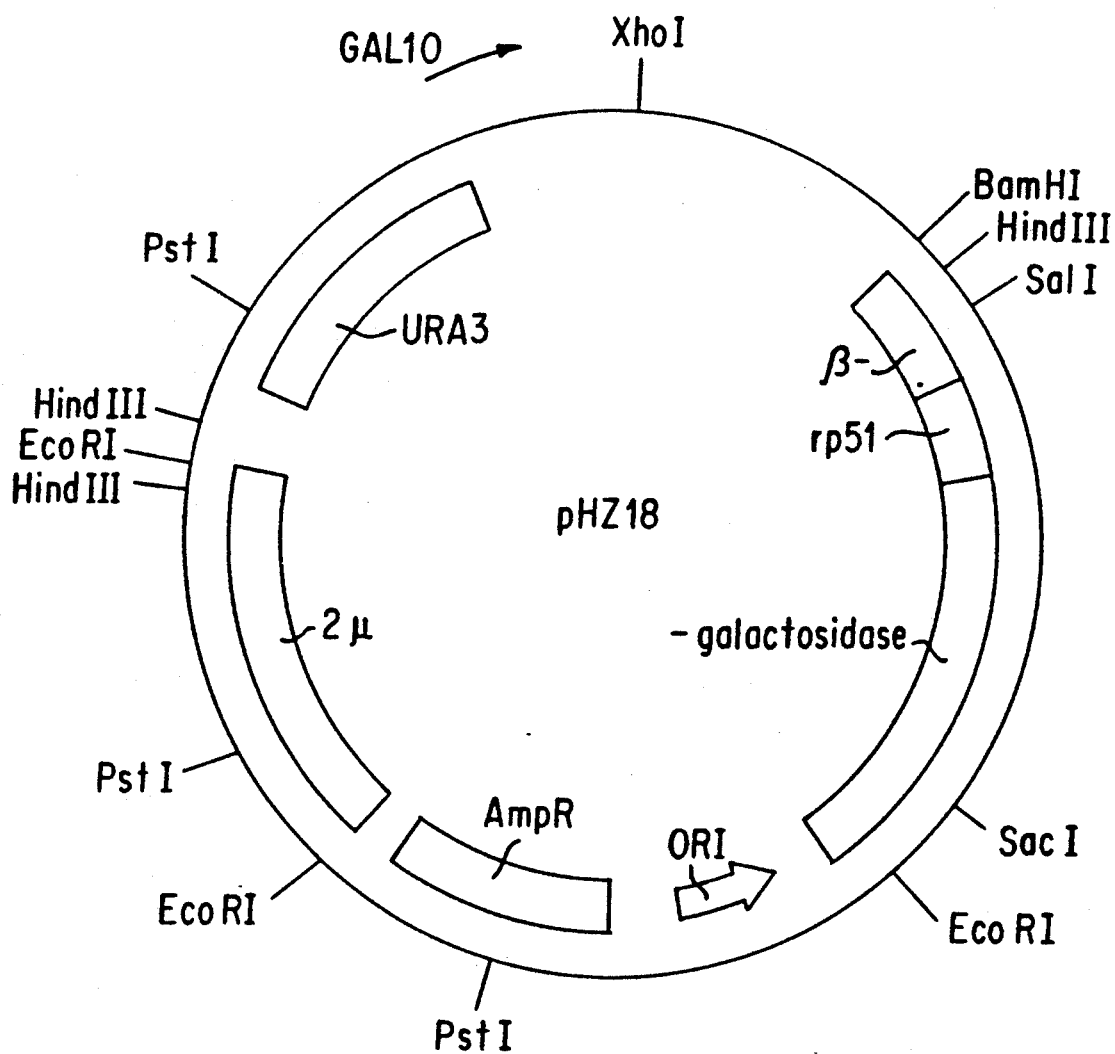
FIG. 1 depicts the restriction map of the plasmid pHZ18. See, Roshbash, Pro. Natl. Acad. Sci. USA, 80:4403 (1983).

Antifungal agents act by various mechanisms. One type of antifungal agent causes perturbations in the fungal cell wall or membrane (i.e., a weakened or discontinuous cell envelope). The method of the invention allows for screening test compounds for this type of antifungal activity.

To detect these perturbations, fungal cells (S. cerevisiae) were constructed which place the E. coli $\beta$-galactosidase gene under the control of the S. cerevisiae galactose regulatory system. When these strains were grown in the presence of glucose and galactose, the $\beta$-galactosidase gene was not expressed. Glucose inhibited the entry of galactose into the cell—a phenomenon referred to as "inducer exclusion"—and thereby prevented the activation of the galactose regulated genes. If however a test compound causes a breach in the cell envelope, galactose can enter and induce the synthesis of $\beta$-galactosidase. This enzyme causes development of the $\beta$-galactosidase indicator such as 5-bromo-4-chloro-3-indolyl-$\beta$-D-galactopyranoside (XG) resulting in a deep blue color. The system is sensitive enough to detect color formation resulting from the action of glucan synthetase inhibitors in the absence of a zone of growth inhibition. It is specific enough that compounds that interfere with membrane function (e.g., polyenes) yield clear zones without color. Thus, a specific, quick, sensitive and easy to read system is provided.

$\beta$-galactosidase is an enzyme that reacts with numerous galactose containing substrates, cleaving the galactose from the rest of the molecule. Several of these substrates produce a deep color upon cleavage (e.g., 5-bromo-4-chloro-3-indolyl-$\beta$-D-galactopyranoside) or a fluorescent product upon said cleavage (e.g., methylumbelliferyl-$\beta$-D-galactopyranoside). The present invention seeks to take advantage of this colorimetric phenomenon by genetically engineering a fungal cell whose $\beta$-galactosidase production is activated by a compound (galactose) which can only enter cells with weakened or discontinuous cell envelopes. Such cells, when grown in media containing a $\beta$-galactosidase reactive colorimetric indicator, would produce color when reacted with $\beta$-galactosidase, which would only be stimulated upon entry of the activating agent (galactose) into the cell through the deformed cell envelope.

The most commonly used colorimetric assay is based upon the E. coli $\beta$-galactosidase and its indicator substrate, 5-bromo-4-chloro-3-indolyl-$\beta$-D-galactopyranoside (XG). Cleavage of XG by $\beta$-galactosidase yields an intense blue pigment, which is very easy to detect. When the gene for this enzyme is placed downstream from a yeast promoter, the synthesis of $\beta$-galactosidase and, hence, the production of blue yeast cells is directly tied to the regulatory elements controlling that promoter. Other genes placed in the same location as the substituted gene would produce similar colorimetric results if the substituted gene codes for a cleavage enzyme specific for a colorimetric indicator located in the media. Such enzymes may be referred to as indicator cleavage enzymes.

For example, the lacZ gene, which codes for β-galactosidase, could be replaced by the *S. cerevisiae* ADE2 genes, which codes for PR-aminoimidazole carboxylase (Jones and Fink, *The Molecular Biology of the Yeast Saccharomyces—Metabolism and Gene Expression*, Cold Spring Harbor (1982), p. 271). This reference is hereby incorporated by reference.

Three major aspects of the galactose regulatory system are involved in the present invention. The first is the induction of the galactose metabolizing enzymes by galactose itself. The GAL4 gene product is a positive regulator of the galactose structural genes, and it is required for transcription of these genes. The GAL80 gene product is a negative regulator of the system. In the absence of intracellular galactose, the GAL80 protein is believed to interact with the GAL4 protein and form an inactive complex. The presence of galactose breaks down this complex. The GAL4 protein can then promote transcription of all the galactose regulated structural genes.

Second, the GAL2 gene encodes the galactose-specific permease and is itself under galactose-inducible regulation. Thus, when galactose is absent, little or no permease is synthesized. Permease is synthesized when this system is induced by galactose. This allows more galactose to be actively transported into the cell in an autocatalytic manner.

The third aspect is the effect glucose exerts on the system. It appears that the presence of glucose blocks the expression of the galactose inducible genes at two points. First, at the cell surface, an "inducer exclusion" mechanism prevents the uptake of galactose from the medium. The second blockage point is at the transcriptional level of the galactose structural genes. Whenever glucose is present, at least two negative regulatory proteins (encoded by the GAL82 and GAL83 genes) act to inhibit the expression of these galactose inducible genes.

When an indicator cleavage enzyme gene is placed under the control of a GAL promoter in a fungal cell, such as *Saccharomyces cerevisiae*, which has been grown with both glucose and galactose in the medium, the GAL promoter is not induced. As a result, the indicator cleavage enzyme is not synthesized and the cells maintain their white phenotype. If galactose is present as the sole carbon source, or if galactose can penetrate the cell in the presence of glucose, transcription initiating from the GAL promoter will lead to the expression of the indicator cleavage enzyme. This will elicit the formation of blue color.

Below, techniques for making and using a culture of fungal cells containing a genetically engineered marker gene in a colorimetric assay to determine cell envelope perturbations are discussed in general terms. In addition, several embodiments are described wherein the general techniques are applied using specific promoters, plasmids, culture media, and incubation conditions. These embodiments are not intended to be exhaustive; they merely illustrate the invention so that one skilled in the art is able to make and use the assay system. Colorimetric assay is defined as any assay which evidences a positive reaction by the production of a colorimetric indicator emitting or reflecting detectable and identifiable electromagnetic radiation. Although the most easily detected radiation is in the form of reflected visible light, it could also be the result of fluorescence, phosphorescence or luminescence. Indicator cleavage enzymes are polypeptides, coded by a gene, and capable of reacting with an associated indicator to produce a colorimetrically detectable product. This invention is intended to include within its scope the use of all indicators capable of being developed in response to an indicator cleaving enzyme that has been placed downstream from the galactose regulatory elements. Preferred indicators are capable of being developed in response to β-galactosidase, e.g. indicators capable of covalently bonding to galactose or derivatives thereof and being cleaved therefrom by β-galactosidase.

Vectors

The vectors employed in this invention contain an indicator cleaving enzyme gene downstream from a promoter that is preferably inducible by galactose. The promoter may be a fungal promoter or any promoter that is functional in the fungal organism. In addition, there may be other regulatory genes which inhibit the expression of indicator cleaving enzyme in the absence of galactose or enhance it in the presence of galactose. The vector may also contain any convenient marker for selecting successfully transformed fungal cells e.g. G418 resistance or uridine biosynthetic genes. For example, a vector containing a gene or genes conferring resistance to a usually lethal agent, when placed in an organism lacking such resistance, will select only successfully transformed microbes when grown on a medium containing the lethal agent.

The method of constructing such plasmids are well known to one skilled in the art. The source of β-galactosidase is most often *E. coli*, but may be from a number of sources. The marker selected may also be from any of a number of sources. More specific examples are provided below.

pHZ18 (FIG. 1) is a defective 2 micron based bifunctional plasmid (replicates in *S. cerevisiae* and *E. coli*) constructed by M. Rosbash (Proc. Nat. Acad. Sci. USA, 80: 4403 (1983)). This reference is therefore incorporated by reference herein for its pertinent teachings. As such, the plasmid can only replicate in yeast strains that already have an endogenous 2 micron plasmid. The copy number of pHZ18 is probably somewhere between 10 and 50 per cell. pHZ18 contains the *E. coli* β-galactosidase gene into which a yeast intron has been engineered. It is transcribed from the GAL10 promoter. It carries the URA3 gene as a selective marker when transforming ura3 mutants.

Other constructs utilizing the β-galactosidase gene under galactose regulation would also be useful in the assay system of this invention, particularly those utilizing the GAL1 promoter. This promoter may be four times as strong as the GAL10 promoter found in pHZ18 or pT1404 described elsewhere (there is approximately four times as much of the GAL1 gene product relative to the GAL10 gene product in *S. cerevisiae*).

Figure 2:
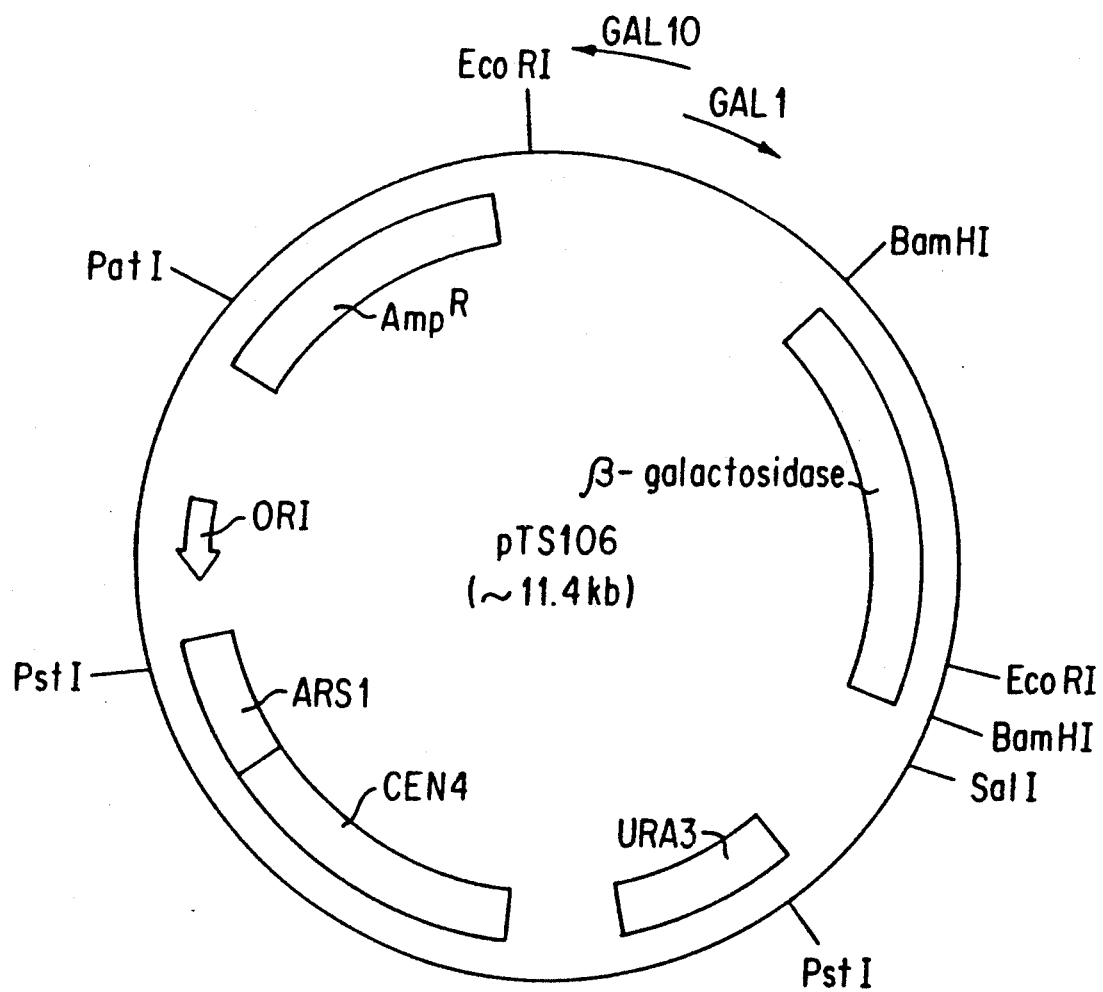
FIG. 2 depicts the restriction map of the plasmid pHZ106. Pedigree: - galactosidose cloned into pBM150.
Figure 3:
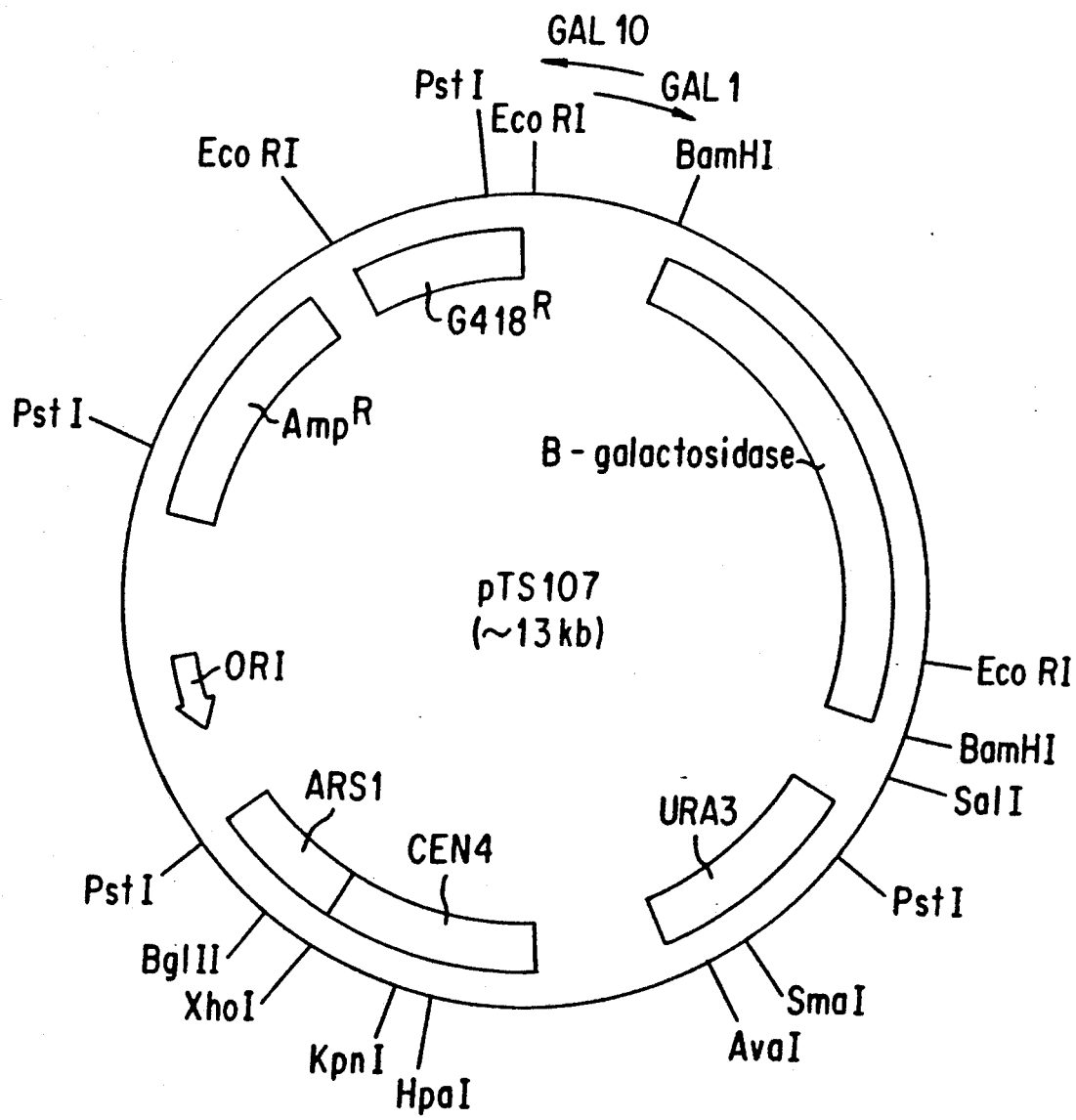
FIG. 3 depicts the restriction map of the plasmid pTS107. Pedigree: G418 resistance gene cloned into pTS106.

For example, pTS106 (FIG. 2) is a single copy, CEN4 ARS1, bifunctional plasmid that carries URA3 as a selectable marker. It has the *E. coli* β-galactosidase, under galactose regulation, transcribed from the GAL1 promoter. pTS107 (FIG. 3) is another GAL1 promoter containing plasmid that is the same as pTS106 except that it carries a gene which confers resistance to G418 as well (G418R).

Hosts

A similarly engineered plasmid may be prepared for use in other fungi by techniques within the skill of the art. *S. cerevisiae* was chosen as the model fungus to test this system because of its well-documented genetics, the existence of workable cloning systems, and the overall ease with which it can be manipulated. The DBY-689 host strain is a common, well characterized laboratory strain. The structural genes encoding the galactose metabolizing enzymes are induced a thousand-fold over basal levels by the presence of intracellular galactose. When glucose is present, another set of regulatory proteins comes into play and represses any expression of genes involved in galactose metabolism, even if galactose is also present in the media. Similar systems could be constructed in any number of fungi as more information and cloning systems become available.

Transformation

A number of transformation procedures common in the field of genetic engineering that are well known to those skilled in the art may be used. The best results obtained for the present invention utilized the lithium acetate or spheroplast yeast transformation procedures. For examples, see, Gray et al., Proc. Nat. Acad. Sci. USA, 79 : 6598 (1982) for transformation of *E. coli* and Hinnen et al., Proc. Nat. Acad. Sci. USA, 75: 1929 (1978) for transformation of yeast. These articles are hereby incorporated by reference for their pertinant teachings.

Media

The transformed fungal cells can be grown by any conventional means, e.g. on any conventional sustaining medium. The medium may contain or be deficient in a component or element which is complementary to engineered gene markers as discussed above.

The medium will also contain the colorimetric indicator, an uptake inhibitor such as glucose and an activator such as galactose. The colorimetric indicator will be present in an amount effective to produce a colorimetric response to the production of indicator cleavage enzyme by the transformed fungal cells. Preferably, the response is specific, sensitive and rapid. The uptake inhibitor will be present in an amount effective to inhibit penetration of the activator through the fungal cell wall in the absence of a cell wall perturbation caused by a test compound or test sample. The activator should be present in an amount effective to activate the fungal promoter and to allow the activator and the colorimetric indicator to penetrate through the fungal cell wall in the absence of the uptake inhibitor. The ratio of activator to uptake inhibitor is preferably in the range of 1.5:1 to 1:1.5 by weight, and more preferably in the range of 1.2:1 to 1:1.2, and most preferably about 1:1.

The Assay

The assay is performed by placing the transformed fungal cell in the medium e.g. by streaking, swabbing, etc. and then spotting a test compound or test sample on the medium, preferably at a specific predetermined point. The medium is then incubated for a suitable time to allow perturbation of the cell envelope by the test material, penetration of galactose through the cell wall, activation of the fungal promoter by galactose, production of indicator cleavage enzyme by the fungal cell and development of the indicator. Incubation preferably should be brief enough to avoid development of significant background color. Suitable incubation times are usually from 1 to 5 days, depending upon the temperature, culture medium etc. Usually about three days incubation at about 30° C. is employed. The indicator as discussed above can be detected by various means; preferably it is a visible indicator.

MATERIALS AND METHODS

Preparation of XG Indicator Plates for Use in Assay

The XG indicator plates were agar plates containing a number of salts, vitamins and amino acids. They also contained the indicator 5-bromo-4-chloro-3-indolyl-$\beta$-D-galactopyranoside (final concentration of 40 $\mu$g/ml) and about 2% sugar (glucose and galactose). A glucose:galactose ratio of about 1:1 yielded the best results; a significant impact upon the assay only occurred when all sugar was in the form of galactose, which produced a light blue background throughout the media. The XG indicator plates contained the following. XG is normally made up as a 20 mg/ml stock solution in dimethyl formamide and 2 ml of this added per liter of medium to yield the 40 $\mu$g/ml final concentration.

| XG indicator plates | |
|---|---|
| agar | 20 gm. |
| distilled water | 700 ml. |
| post sterile additions: | |
| 40% sugar | 50 ml. |
| 5X "XG" salts | 200 ml. |
| 20 mg/ml XG in DMF | 2 ml. |
| 20X supplements | 50 ml. |
| 100X vitamins | 10 ml. |
| 5X "XG" salts: | |
| Potassium Phosphate (monobasic) | 68 gm. |
| Ammonium Sulfate | 10 gm. |
| Potassium hydroxide | 21 gm. |
| 0.4M Magnesium sulfate | 10 ml. |
| 0.001M Ferric sulfate | 10 ml. |
| Adjust the pH to | 7.0 |
| distilled water | 1000 ml. |
| 100X vitamins: | |
| Thiamine | 40 mg. |
| Pyridoxine | 40 mg. |
| Pantothenic acid | 40 mg. |
| Inositol | 200 mg. |
| Biotin | 2 mg. |
| Distilled water | 1000 ml. |
| 20X Supplements (also known as 20X Dropout Solution): | |
| Adenine sulfate | 0.4 gm. |
| Arginine HCl | 0.8 gm. |
| Histidine HCl | 0.4 gm. |
| Isoleucine | 1.2 gm. |
| Leucine | 1.2 gm. |
| Lysine HCl | 1.0 gm. |
| Methionine | 0.4 gm. |
| Phenylalanine | 1.0 gm. |
| Threonine | 4.0 gm. |
| Tryptophan | 0.8 gm. |
| Tyrosine | 1.0 gm. |
| *Uracil | 0.4 gm. |
| distilled water | 1000 ml. |

*This is not added normally when ura3 strains are used with URA3 marked plasmids.

Colorimetric Assay Procedure

The *S. cerevisiae* were transformed with the appropriate vector (e.g. pHZ18) by the procedure of Hinnen et al., Proc. Natl. Acad. Sci. USA, 75:1929 (1978). Cultures of strains were scraped from a fresh selective plate (lacking uracil) and resuspended in water to an optical density of about 20 (i.e., a 1:50 dilution that has an OD of 0.4 when measured at 660 nm on a Beckman DB-GT spectrophotometer). 0.1 ml of this cell suspension was spread on XG indicator plates (lacking uracil) with a sterile cotton swab. Test compounds were always dissolved in DMSO at a concentration of 1 mg/ml except: G418 in water; cyclohexamide and cerulenin in ethanol; benomyl in DMSO at 2 mg/ml. The sample solutions were spotted on round 6.5 mm diameter pieces of filter paper and allowed to dry at room temperature for at least one hour before being placed on the freshly seeded lawn. Incubation periods ranged up to about 14 days at 30° C. After such a period, the glucose in the media becomes depleted and the entire lawn becomes blue. Best results were obtained at 30° C. with incubation times of 3-5 days.

RESULTS gal80 vs. GAL80 Strains to Demonstrate the Galactose Inducibility of the GAL10 Promoter To demonstrate that the system is under the control of the GAL regulatory system, a series of experiments were performed. One possible system for employing galactose permeation as an indicator of cell wall dysfunction included the use of gal80 mutants. These are defective in a negative regulatory protein that represses the synthesis of galactose-metabolizing genes. Towards this end two gal80 ura3 yeast host strains, designated TS12 and TS7 were constructed using standard genetic methods.

Figure 4:
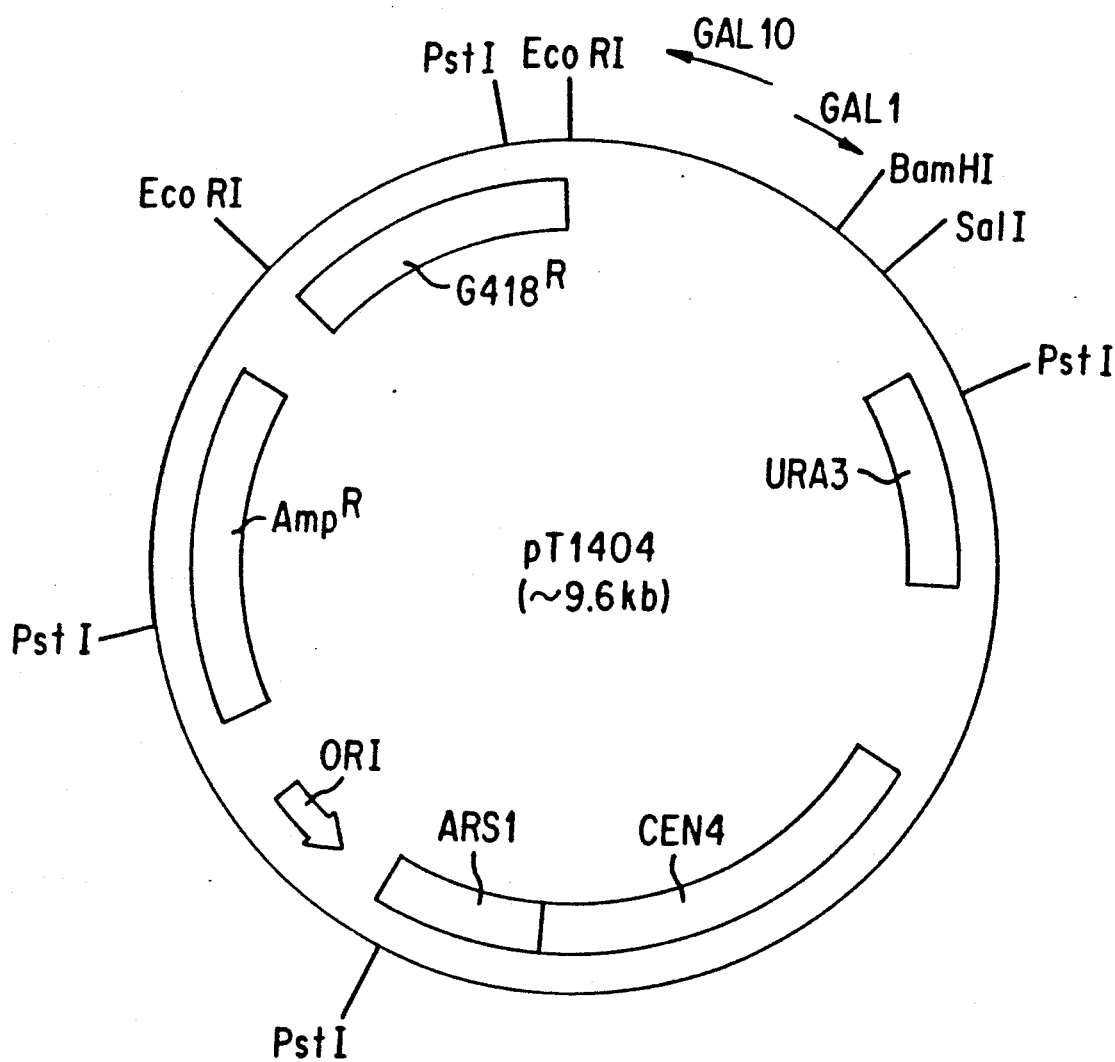
FIG. 4 depicts the restriction map of the plasmid pT1404, which was used to establish the utility of the present invention. Pedigree: G418 resistance gene cloned into pBM150.
Figure 5:
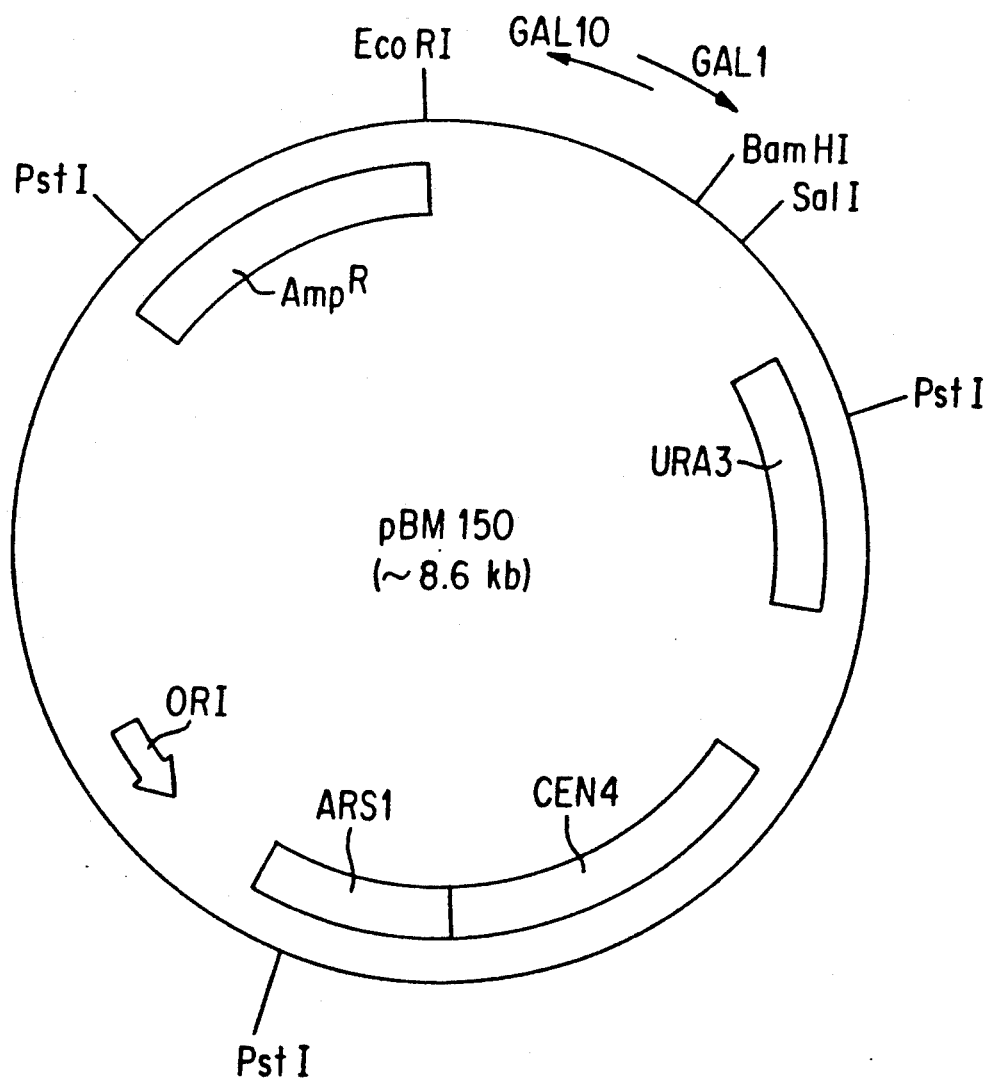
FIG. 5 depicts the restriction map of the plasmid pBM150, which was used to construct the plasmid pT1404. Johnson, M. et al. Mol. Cell. Bio. 4:1440 (1984).

Confirmation that the gal80 mutant would in fact yield an increased level of galactose regulated gene products when grown under non-inducing conditions, was obtained by studying the expression of a GAL10 promoter-dependent G418 resistance marker. A 2'-0-phosphotransferase gene (conferring G418 ®) was subcloned downstream of the GAL10 promoter on a centromere containing vector to yield pT1404 (FIG. 4). pT1404 is a single copy, CEN4 ARS1 containing bifunctional replicon. It carries URA3 and G418-resistance (G-418 ®) as selective markers. It was derived from pBM150 (FIG. 5) by insertion of an Eco RI fragment that carries a gene encoding an aminoglycoside 2'-0-phosphorylating enzyme. This gene confers G418 ® in S. cerevisiae when placed downstream of a functional promoter. The recombinant plasmid, pT1404 (FIG. 4), was then used to transform the three yeast strains described above: DBY689 (GAL80), TS12 (gal80), and TS7 (gal80). All three parental strains could grow on complex media containing either glucose or galactose as the carbon source. Transformants of DBY689 (GAL80) carrying pT1404 were resistant to G418 on galactose containing media but were sensitive to G418 when glucose was the carbon source. This indicates that the resistance gene was under galactose regulation. In contrast, the two gal80 mutants TS12 and TS7 were resistant to G418 whether the plates contained glucose or galactose. This demonstrates that glucose repression had been partially bypassed.

The projected indicator enzyme, the E. coli β-galactosidase, was then introduced into both DBY689 (GAL80) and TS12 (gal80) by transforming each strain with pHZ18. This plasmid carries the E. coli β-galactosidase gene transcribed from the GAL10 promoter.

Analysis of these transformed strains on XG indicator plates showed that DBY689 was white on glucose media and blue on galactose media as expected. TS12 (gal80) on the other hand, was blue in both cases indicating that a sufficient amount of XG did enter the cell to be converted into the observed blue dye. These initial experiments demonstrated that once the galactose regulated genes were induced (e.g. via the gal80 mutation), glucose catabolite repression (mediated by the GAL82, GAL83, and other genes) was not absolute.

DBY689 (and its derivatives carrying pHZ18) grew very slowly on galactose media. Healthy, deep blue colonies of DBY689/pHZ18 that finally grew upon the XG-galactose indicator plates were purified and verified to still be GAL80. These were designated GAUHZ-1 (for galactose utilizing, pHZ18) and were used in subsequent experiments. A derivative of GAUHZ-1 was isolated that had lost the pHZ18 plasmid after growth under non-selective conditions. This strain, "cured" of pHZ18, was designated GAU-1.

Survey of Compounds Using GAUHZ-1

The first screen was done using GAUHZ-1 as the indicator strain upon which twenty-four substances (many with known antifungal activities) were disc tested. The observed zone diameters (Table I) were comparable to previously recorded data with other S. cerevisiae strains. The only active, characterized cell wall synthesis inhibitor in this screen (aculeacin) displayed a deep blue ring around the edge of the observed zone of inhibition. This color was detected at a number of glucose to galactose ratios (even at 1.3% glucose:0.7% galactose) suggesting that the influence of glucose from the potential natural product fermentation broths might not be detrimental. Even on 2% galactose plates (with no glucose), where the entire lawn had a blue tint, the dark blue ring around the aculeacin zone of inhibition was clearly visible. Furthermore, no significant color was observed with the other known antifungal actives such as polyenes and imidazoles.

Improved Indicator Strains

Within the overall blue ring surrounding the aculeacin zone, a number of colonies were observed that were a much deeper blue than their siblings. These were picked, purified and designated ASB mutants (aculeacin super blue). Of the ten that were retained, ASB13 exhibited the deepest blue color in the shortest period of time. Similarly, a number of deep blue variants were observed within the lawn seeded on plates containing discs spotted with imidazole derived compounds. A number of these were also isolated and designated ZSB mutants (imidazole super blue). Plasmid DNA has been isolated from each of these mutants, transferred to E. coli, amplified, reisolated and transformed back into GAU-1, the plasmid-free yeast host described above. None of these S. cerevisiae transformants exhibited the "super blue" phenotype indicating that the mutations were in the original host strains and not in the plasmid.

TABLE I

| | Survey of Knowns vs. GAUHZ-1 at Different Glucose:Galactose (Glu:Gal) Ratios | | | | | | | |
|---|---|---|---|---|---|---|---|---|
| | 1% Glu:1% Gal | | 1.3% Glu:0.7% Gal | | 1.6% Glu:0.4% Gal | | 2% Gal | |
| Compound | Zone | Comment | Zone | Comment | Zone | Comment | Zone | Comment |
| 1. triclosan | ± | | ± | | 10.1 | | 12.9 (21.1) | C |
| 2. chlotrimazole | 12.0 | | 14.0 | | 11.7 | | 0 (25.7) | C |
| 3. pantricin CH₃ ester | 13.9 | A | 14.8 | | 15.0 | | 22.2 | |

TABLE I-continued

Survey of Knowns vs. GAUHZ-1 at Different Glucose:Galactose (Glu:Gal) Ratios

| Compound | 1% Glu:1% Gal | | 1.3% Glu:0.7% Gal | | 1.6% Glu:0.4% Gal | | 2% Gal | |
|---|---|---|---|---|---|---|---|---|
| | Zone | Comment | Zone | Comment | Zone | Comment | Zone | Comment |
| 4. Loprox | 12.7 | A | 11.0 | A | 10.0 | | 17.1 | |
| 5. miconazole | 14.8 | | 15.8 | | 14.2 | | 13.6 (24.3) | C |
| 6. tioconazole | 38.9 | | 37.3 | | 37.4 | | 50.4 (50.4) | C |
| 7. IW85-190 (allylamine) | 0 | | 0 | | 0 | | 0 | |
| 8. griseofulvin | 0 | | 0 | | 0 | | 0 | |
| 9. omoconazole | 10.8 | | 12.0 | | 11.6 | | 0 (26.5) | C |
| 10. pimaricine | 0 | | 0 | | 0 | | 0 | |
| 11. econazole | 20.0 | | 23.2 | | 17.4 | | 0 (35.5) | C |
| 12. nystatin | 0 | (A) | 0 | | 0 | | 0 | |
| 13. bifonazole | 10.2 | | 0 | | ± | | 16.2 (31.0) | C |
| 14. ketoconazole | 15.0 | | 14.3 | | 14.0 | | 0 (28.5) | C |
| 15. oxiconazole | 18.7 | | 22.2 | | 21.8 | | 0.5 (38.6) | C |
| 16. tolciclate | 0 | | 0 | | 0 | | 0 | |
| 17. candicidin | 16.6 | | 14.7 | | 15.8 | | 28.2 | |
| 18. tolnaftate | 0 | | 0 | | 0 | | 0 | |
| 19. naftifine | 0 | | 0 | | 0 | | 0 | |
| 20. sodium dodecyl sulfate | 0 | | 0 | | 0 | | 0 | |
| 21. polyoxin D | 0 | | 0 | | 0 | | 0 | |
| 22. aculeacin | 13.9 | B | 16.0 | B | 16.7 | A | 17.1 | B |
| 23. dimethyl sulfoxide | 0 | | 0 | | 0 | | 0 | |
| 24. G418 | 0 | | 0 | | 0 | | 0 | |

A = minor light blue ring at edge of the zone
B = intense, sharp blue ring at edge of the zone
C = no zone per se but a white area within a blue background Survey of Compounds--GAUHZ-1 vs. ASB13

An end point comparison was made for the appearance of blue color and a measurable zone between ASB13 and its immediate parent GAUHZ-1 using two known inhibitors of glucan synthetase, aculeacin A and papulacandin B. The results (Table II) show that ASB13 will exhibit a blue color with papulacandin B even when no zone of inhibition could be detected. The blue color seen using ASB13 is much deeper than that with GAUHZ-1 and is observable in a shorter period of time. ASB13, as shown below as well, is not more sensitive to antibiotics than its parent—it is simply a better colorimetric indicator strain. ASB13 is merely the thirteenth of many aculeacin super blue strains that were isolated. Any of the other strains would produce the accelerated color change, such that one skilled in the art need only pick and purify any of the darker ASB colonies within the blue zone to obtain substantially the same results.

TABLE II

| Compound/Strain | µg of compound | Detection of Color | Detection Zone |
|---|---|---|---|
| Papulacandin C/ASB13 | 0.5 | + | 0 |
| | 0.75 | + | + |
| Papulacandin C/GAUHZ-1 | 0.75 | 0 | + |
| | 2.5 | + | + |
| Aculeacin A/ASB13 | 2.5 | + | + |
| Aculeacin A/GAUHZ-1 | 2.5 | + | + |

Table III summarizes the results of a test of ASB13 and its immediate parent GAUHZ-1 when subjected to a disc assay test with 10 micrograms of each compound.

TABLE III

| Compound | ASB13 | | GAUHZ-1 | |
|---|---|---|---|---|
| | Zone | Comment | Zone | Comment |
| 1. triclosan | 7.1 | | 10.2 | |
| 2. chlortrimazole | 8.5 | C | 12.2 | |
| 3. patricin CH₃ ester | 15.6 | | 15.5 | |
| 4. Loprox | 12.3 | | 7.2 | |
| 5. miconazole | 10.3 | C | 18.8 | |
| 6. tioconazole | 32.2 | C | 31.8 | A |
| 7. IW85-90 (allylamine) | 0 | | 0 | |
| 8. griseofulvin | 0 | | 0 | |
| 9. omoconazole | 0 | C | 10.1 | |
| 10. primacine | 0 | | 0 | |
| 11. econazole | 12.5 | C | 23.4 | |
| 12. nystatin | 12.0 | | 10.1 | |
| 13. bifanazole | 0 | C | 9.5 | |
| 14. amphotericin B | 6.6 | | 7.3 | |
| 15. ketoconazole | 12.3 | C | 6.2 | |
| 16. oxaconazole | 14.0 | C | 23.4 | |
| 17. tolciclate | 0 | | 0 | |
| 18. candicidin | 16.0 | | 17.4 | |
| 19. tolnaftate | 0 | | 0 | |
| 20. naftidin | 0 | | 0 | |
| 21. sodium dodecyl sulfate | 0 | | 0 | |
| 22. polyoxin D | 0 | | 0 | |
| 23. aculeacin A | 13.1 | D | 18.2 | B |
| 24. dimethyl sulfoxide | 0 | | 0 | |
| 25. G418 | 0 | | 0 | |
| 26. papulacandin B | 18.4 | D | 25.0 | B |
| 27. LY 121019 | 7.3 | D | 8.5 | B |
| 28. mitomycin C | 0 | | 0 | |
| 29. cyclohexamide | 0 | | 0 | |
| 30. cerulenin | 23.9 | E | 28.0 | B |
| 31. tunicamycin | 9.3 | | 13.5 | |

A = very slight hint of blue ring within lawn at edge of zone
B = slight blue at edge of sharp zone
C = diffuse blue, wide band in lawn outside of the area of growth inhibition
D = extremely intense, sharp blue band in the immediate vicinity of disc or at zone edge
E = combination of C + D The results of this screen show that ASB13 did exhibit a much deeper blue color in the presence of glucan synthetase inhibitors than its parent GAUHZ-1. The color produced by cerulenin can be avoided by isolating resistant mutants or by reading the plates after only 3 days of incubation. ASB13 also demonstrated a wide, relatively diffuse pale blue haze in the presence of some imidazole derived antimycotic compounds. The morphology of the blue zones induced by the cell wall inhibitors tested is clearly distinguishable from that of the membrane function inhibitors. When plates were examined after only three days, the wall inhibitors still showed deep blue rings on ASB13 but the imidazole (and even cerulenin) induced color was barely detectable.

Glucose:Galactose Ratio

The effect of the presence of both glucose and galactose on β-galactosidase induction was also examined. For both GAUHZ-1 and DBY689/pHZ18 the lawns were white with either a mixture of 1.6% glucose:0.4% galactose or 1% glucose:1% galactose. A slight blue coloration was noted at a combination of 0.4% glucose:1.6% galactose in the plates. The combination of glucose catabolite repression and normal galactose gene regulation, therefore, was tight enough to serve as the basis of the proposed assay system. As shown in Table IV, in most cases, the pale blue imidazole-specific zones did increase in intensity with increasing levels of glucose in the medium. The deep blue, sharp ring produced by the action of papulacandin B, aculeacin A, and LY121019 (an echinocandin B-like experimental compound obtained from Eli Lilly) was still retained, however.

supernatants were spotted onto discs and allowed to dry. The discs were then over-spotted with 10 microliters of a 1 mg/ml stock of either papulacandin or candicidin. Three glucose to galactose ratios were tested (1% glucose:1% galactose, 0.8% glucose:1.2% galactose, 0.6% glucose:1.4% galactose). The results indicated that the fermentation supernatants do not interfere with this assay system.

The plates with the preferred 1% glucose:1% galactose mixture yielded deep blue colors on a white background in the presence of papulacandin. Increasing the levels of galactose to counteract the excess glucose from the fermentation broth was not necessary. In fact the excess galactose seemed to increase the "noise" level of the system in that the entire lawn turned a light blue.

In the second approach, 0.1 ml of a select group of fermentation supernatants were added to 6.5 mm diameter wells that had been cut into agar plates with a #2 cork borer. The samples were spiked with papulacandin or candicidin to final concentrations of 100 μg/ml each. Again, the fermentation supernatants did not interfere with the assay system.

The idea that non-lethal "holes" are being generated over a finite inhibitor concentration range is supported by a number of observations. The first is that addition of

TABLE IV

| Screen vs. ASB13 at Different Glucose:Galactose (Glu:Gal) Ratios | | | | | | |
|---|---|---|---|---|---|---|
| | 1% glu:1% gal | | 1.2% glu:0.8% gal | | 1.4% glu:0.6% gal | |
| Compound | Zone | Comment | Zone | Comment | Zone | Comment |
| 1. triclosan | 0 | | 6.5 | | 6.6 | |
| 2. chlortrimazole | 0 | A | 0 | <A | 0 | =A |
| 3. patricin CH$_3$ ester | 15.4 | | 14.5 | | 14.6 | |
| 4. Loprox | 8.4 | | 9.5 | | 10.7 | |
| 5. miconazole | 10.7 | A | 8.8 | =A | 7.3 | =A |
| 6. ticonazole | 24.4 | A | 19.0 | =A | 25.4 | =A |
| 7. IW85-190 (allylamine) | 0 | | 0 | | 0 | |
| 8. griseofulvin | 0 | | 0 | | 0 | |
| 9. SCH 28191 | 0 | | 0 | | 0 | |
| 10. omoconazole | 7.5 | A | 0 | <A | 0 | <A |
| 11. primacine | 0 | | 0 | | 0 | |
| 12. econazole | 10.2 | A | 0 | <A | 0 | <A |
| 13. nystatin | 10.6 | | 9.6 | | 10.7 | |
| 14. bifonazole | 7.5 | A | 0 | <A | 0 | <A |
| 15. amphotericin B | 0 | | 6.7 | | 0 | |
| 16. ketoconazole | 7.5 | A | 8.5 | <A | 8.7 | <A |
| 17. oxiconazole | 13.4 | A | 11.0 | <A | 12.8 | <A |
| 18. tolciclate | 0 | | 0 | | 0 | |
| 19. candicidin | 17.7 | | 18.5 | | 15.9 | |
| 20. tolnaftate | 0 | | 0 | | 0 | |
| 21. naftidin | 0 | | 0 | | 0 | |
| 22. polyoxin D | 0 | | 0 | | 0 | |
| 23. aculeacin | 13.6 | B | 12.0 | =B | 12.8 | =B |
| 24. dimethyl sulfoxide | 0 | | 0 | | 0 | |
| 25. G418 | 0 | | 0 | | 0 | |
| 26. Papulacandin B | 18.7 | B | 16.4 | =B | 18.9 | =B |
| 27. LY121019 | 7.5 | B | 6.8 | =B | 0 | =B |
| 28. mitomycin C | 0 | | 0 | | 0 | |
| 29. cycloheximide | 0 | | 0 | | 0 | |
| 30. cerulenin | 22.8 | C | 23.4 | <C | 22.1 | =C |
| 31. tunicamycin | 13.1 | | 10.5 | | 11.5 | |
| 32. benomyl | 0 | | 0 | | 0 | |
| 33. logonin | 21.5 | | 19.3 | | 21.0 | |

A = broad, pale blue hazy area around a "zone" of inhibition (<or = indicates color relative to the preceeding, lower level of glucose)
B = intense, sharp distinct deep blue ring around a zone of inhibition
C = a combination of A + B - fairly intense blue but a relatively wider band Effect of Natural Product Fermentation Broth Supernatants Two approaches were taken to evaluate the influence of natural product fermentation supernatants on the galactose permeation system. In the first experiment, 25 microliters of eighteen different fermentation broth sorbitol to the medium as an osmotic stabilizer eliminates the production of blue color even though zones of growth inhibition were still observed with aculeacin and papulacandin. (Apparently, under the conditions employed in this experiment S. cerevisiae is not able to grow as a spheroplast). We have been able to isolate and purify deep blue colonies from within the color ring surrounding aculeacin discs indicating that they were indeed viable and that the color was not generated by cell lysis and liberation of the β-galactosidase. These clones also continued to exhibit the phenotype (hyperproduction of color) for which they were picked. Finally, XG was relatively unable to penetrate *S. cerevisiae*. Even when the assays were conducted using 2% galactose and no glucose in the plates, deeper blue rings were visible within a lighter blue lawn.

Although the invention has been explained above using galactose and glucose as examples of the activator and uptake inhibitor materials, respectively, other materials having similar effects in the fungal cell system can be employed. For example, galactose and glucose analogs or derivatives such as methylated galactose and fructose may also be suitable.

The descriptions of the foregoing specification have been presented for the purpose of illustration and description. Obviously, many modifications and variations are possible in light of the above teachings. The specification is intended to best explain the principles of the invention and its practical application and to enable others skilled in the art to best utilize the invention in various embodiments and with various modifications as are suited to the particular use contemplated.

We claim:

1. A colorimetric assay for detecting a discontinuous fungal cell envelope comprising:
    a. placing a test compound or test sample being assay for antifungal activity on or in a culture medium comprising (1) a colorimetric indicator, (2) a fungal cell transformed with a vector containing an indicator cleavage enzyme gene downstream from a fungal promoter, said indicator cleavage enzyme gene coding for a cleavage enzyme specific for said colorimetric indicator, (3) an activator material that activates said fungal promoter and causes expression of the indicator cleavage enzyme by the transformed cell, and (4) an inhibitor material which inhibits the uptake of said activator material through the cell envelope of the transformed cell in the absence of a discontinuous cell envelope;
    b. incubating the culture for sufficient time to enable activation and expression of the indicator cleavage enzyme gene and development of the colorimetric indicator; and
    c. detecting the development of the indicator in said culture medium.

2. The colorimetric assay of claim 1 wherein the indicator cleavage enzyme is β-galactosidase.

3. The colorimetric assay of claim 2 wherein the activator material is galactose and the inhibitor material is glucose.

4. A colorimetric assay for detecting a discontinuous fungal cell envelope comprising:
    a. transforming a fungal cell host with a vector containing a β-galactosidase gene, said gene downstream from a galactose activated fungal promoter subject to galactose regulation in the fungal host;
    b. growing said transformed fungal cells on a sustaining medium comprising sufficient amounts of the sugars glucose and galactose and a colorimetric indicator of β-galactosidase activity, said glucose inhibiting the entry of said galactose into the cell in the absence of a discontinuous cell envelope, and said galactose being capable of activating the galactose activated fungal promotor when present in the cytoplasm of the transformed fungal cell host;
    c. placing a test compound or test sample to be tested for discontinuous cell envelope activity on or in said media culture, said activity allowing entry of galactose into the cell;
    d. incubating the culture for sufficient time to enable activation of β-galactosidase genes and development of the colorimetric indicator; and
    e. detecting the presence of indicator in said media.

5. The colorimetric assay of claim 4 wherein said β-galactosidase gene is from *E. coli*.

6. The colorimetric assay of claim 5 wherein said fungal cells are the yeast *Saccharomyces cerevisiae*.

7. The colorimetric assay of claim 6 wherein said colorimetric indicator of β-galactosidase activity is 5-bromo-4-chloro-3-indolyl-β-D-galactopyranoside or methylumbelliferryl-β-D-galactopyranoside.

8. The colorimetric assay of claim 7 wherein said galactose activated fungal promoter is GAL1 or GAL10.

9. The colorimetric assay of claim 8 wherein the glucose:galactose ratio is at least 1.

10. The colorimetric assay of claim 3 wherein the glucose:galactose ratio is about 1.

11. The colorimetric assay of claim 9 wherein incubation is for a period of at least three days.

12. The colorimetric assay of claim 9 wherein incubation is for a period of about three days.

13. The colorimetric assay of claim 3 wherein said vector comprises the plasmid pHZ18.

* * * * *